US011298050B2

United States Patent
Ikeda

(10) Patent No.: US 11,298,050 B2
(45) Date of Patent: Apr. 12, 2022

(54) POSTURE ESTIMATION DEVICE, BEHAVIOR ESTIMATION DEVICE, STORAGE MEDIUM STORING POSTURE ESTIMATION PROGRAM, AND POSTURE ESTIMATION METHOD

(71) Applicant: Konica Minolta, Inc., Tokyo (JP)

(72) Inventor: Naoki Ikeda, Hino (JP)

(73) Assignee: Konica Minolta, Inc., Tokyo (JP)

( * ) Notice: Subject to any disclaimer, the term of this patent is extended or adjusted under 35 U.S.C. 154(b) by 65 days.

(21) Appl. No.: 16/750,471

(22) Filed: Jan. 23, 2020

(65) Prior Publication Data

US 2020/0245904 A1 Aug. 6, 2020

(30) Foreign Application Priority Data

Jan. 31, 2019 (JP) .............................. JP2019-015905

(51) Int. Cl.
*A61B 5/11* (2006.01)
*G06V 40/20* (2022.01)

(52) U.S. Cl.
CPC ........... *A61B 5/1128* (2013.01); *A61B 5/1116* (2013.01); *G06V 40/23* (2022.01); *G06T 2207/30196* (2013.01)

(58) Field of Classification Search
CPC . A61B 5/1128; A61B 5/1116; G06K 9/00342; G06K 9/00536; G06K 9/00523; G06K 9/6268; G06T 2207/30196
USPC ......................................................... 382/103
See application file for complete search history.

(56) References Cited

U.S. PATENT DOCUMENTS

| | | | | |
|---|---|---|---|---|
| 2012/0162218 A1* | 6/2012 | Kim | ....................... | G06T 19/00 345/419 |
| 2012/0283929 A1* | 11/2012 | Wakita | ..................... | B60N 2/75 701/99 |
| 2013/0265434 A1 | 10/2013 | Iwamoto et al. | | |
| 2014/0127658 A1* | 5/2014 | Rekimoto | .............. | G09B 19/00 434/247 |
| 2015/0169947 A1* | 6/2015 | Kawaguchi | ........ | G06K 9/00335 382/103 |

(Continued)

FOREIGN PATENT DOCUMENTS

JP 2013-232181 A 11/2013

OTHER PUBLICATIONS

Office Action issued in the counterpart European Patent Application No. 20153099.5, dated Jan. 27, 2021 (11 pages).

(Continued)

*Primary Examiner* — Ayodeji O Ayotunde
(74) *Attorney, Agent, or Firm* — Osha Bergman Watanabe & Burton LLP

(57) ABSTRACT

A posture estimation device includes: a processor that: obtains detected information indicating a feature of a subject, wherein the feature is detected based on an image that is captured by an imager from a position where the subject is viewed from above, calculates a feature amount based on the obtained detected information, updates, based on a geometric relationship between the imager and the subject, a model parameter for estimating a posture of the subject by machine learning using the calculated feature amount in a time series, and estimates the posture of the subject using the updated model parameter.

17 Claims, 10 Drawing Sheets

(56) References Cited

U.S. PATENT DOCUMENTS

2016/0278683 A1* 9/2016 Naito .................. A61B 5/1121

OTHER PUBLICATIONS

Tra et al., "Human Fall Detection Based on Adaptive Background Mixture Model and HMM" 2013 International Conference on Advanced Technologies for Communications (ATC 2013), Oct. 1, 2013 (6 pages).

Nicolas Thome et al., "A Real-Time, Multiview Fall Detection System: A LHMM-Based Approach"; IEEE Transactions on Circuits and Systems for Video Technology, vol. 18, No. 11, Nov. 2008 (11 pages).

K.K. Delibasis et al., "Geodesically-corrected Zernike descriptors for pose recognition in omni-directional images"; Integrated Computer-Aided Engineering 23 (2016) 185-199 DOI I0.3233/ICA-160511; (15 pages).

Extended European Search Report issued in corresponding European Application No. 20153099.5, dated Mar. 13, 2020 (11 pages).

\* cited by examiner

A               B

POSTURE ESTIMATION DEVICE, BEHAVIOR ESTIMATION DEVICE, STORAGE MEDIUM STORING POSTURE ESTIMATION PROGRAM, AND POSTURE ESTIMATION METHOD

CROSS-REFERENCE TO RELATED APPLICATION

The entire disclosure of Japanese patent application No. 2019-015905 filed on Jan. 31, 2019, including description, claims, drawings, and abstract, is incorporated herein by reference.

BACKGROUND

1. Technical Field

The present invention relates to a posture estimation device, a behavior estimation device, a storage medium storing a posture estimation program, and a posture estimation method.

2. Description of the Related Art

In Japan, long life has been remarkable due to the improvement of living standards, the improvement of hygienic environment, the improvement of medical standards, and the like accompanying high economic growth after the war. Accordingly, it has become aging society with a high aging rate coupled with a decline in a birth rate. In such aging society, an increase in the number of care receivers and the like requiring care, such as nursing care, is expected due to illness, injury, aging, and the like.

In facilities, such as hospitals and welfare facilities for the elderly, care receivers and the like may fall down while walking or may fall from a bed to be injured. Therefore, in order to ensure that staffs, such as care workers and nurses, are ready to rush when care receivers or the like enter in such a state, there has been developed a technique for detecting postures and behavior of the care receivers or the like from a captured image taken by a camera provided on the ceiling or the like of a room of the care receivers or the like.

In relation to such a technique, there is a technique disclosed in Unexamined Japanese Patent Publication 2013-232181 as a technique for determining, from a captured image, actions or the like of a subject. That is, from a plurality of frames of images output from an imaging device, the situation appearing in the images is recognized on the basis of a recognition process performed on the images, thereby detecting a predetermined event. Then, objects of a type related to the predetermined event are detected from the plurality of frames, and it is determined whether or not the objects are in contact with each other in the real space on the basis of the detected positions of the objects. This makes it possible to interpret events occurred in the video in detail.

SUMMARY

However, with regard to the captured image taken from a position where the subject is viewed from above, due to characteristics or the like of a camera that has taken the captured images, information that can be obtained from the captured images varies depending on a positional relationship or the like between the camera and the subject. Accordingly, accuracy of postures of the subject recognized from the captured images can be reduced. The prior art described above cannot cope with such a matter.

One or more embodiments of the present invention provide a posture estimation device, a behavior estimation device, a storage medium storing a posture estimation program, and a posture estimation method capable of improving detection accuracy of the posture of the subject based on the captured image taken from the position where the subject is viewed from above.

The posture estimation device, the behavior estimation device, the posture estimation program, and the posture estimation of one or more embodiments of the present invention include the followings.

A posture estimation device comprising: an acquisitor that obtains predetermined detected information indicating a feature of a subject detected on the basis of an image captured by an imager from a position where said subject is viewed from above; a feature amount calculator that calculates a predetermined feature amount on the basis of said detected information obtained by said acquisitor; a switcher (an updater) that switches (updates), on the basis of a geometric relationship between said imager and said subject, a model parameter for estimating a posture of said subject by machine learning from said feature amount in a time series calculated by said feature amount calculator; and a posture estimator that estimates said posture of said subject using said model parameter switched by said switcher.

A non-transitory computer-readable storage medium storing a posture estimation program, the posture estimation program causing a computer to perform steps comprising: (a) obtaining predetermined detected information indicating a feature of a subject detected on the basis of an image captured by an imager from a position where said subject is viewed from above; (b) calculating predetermined feature amount on the basis of said detected information obtained in said step (a); (c) switching, on the basis of a geometric relationship between said imager and said subject, a model parameter for estimating a posture of said subject by machine learning from said feature amount in a time series calculated in said step (b); and (d) estimating said posture of said subject using said model parameter switched in said step (c).

A posture estimation method comprising: (a) obtaining predetermined detected information indicating a feature of a subject detected on the basis of an image captured by an imager from a position where said subject is viewed from above; (b) calculating a predetermined feature amount on the basis of said detected information obtained in said step (a); (c) switching, on the basis of a geometric relationship between said imager and said subject, a model parameter for estimating a posture of said subject by machine learning from said feature amount in a time series calculated in said step (b); and (d) estimating said posture of said subject using said model parameter switched in said step (c).

Other features and characteristics of the present invention will become apparent by referring to one or more embodiments exemplified in the following descriptions and the accompanying drawings.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION

Hereinafter, embodiments of the present invention will be described with reference to the drawings. However, the scope of the invention is not limited to the disclosed embodiments.

Hereinafter, a posture estimation device, a behavior estimation device, a posture estimation program, and a method of estimating a posture according to one or more embodiments of the present invention will be described with reference to the accompanying drawings. Note that the same elements are denoted by the same reference signs in the description of the drawings, and duplicate description will be omitted. In addition, dimensional ratios of the drawings are exaggerated for purposes of illustration, and may be different from actual ratios.

Figure 1:
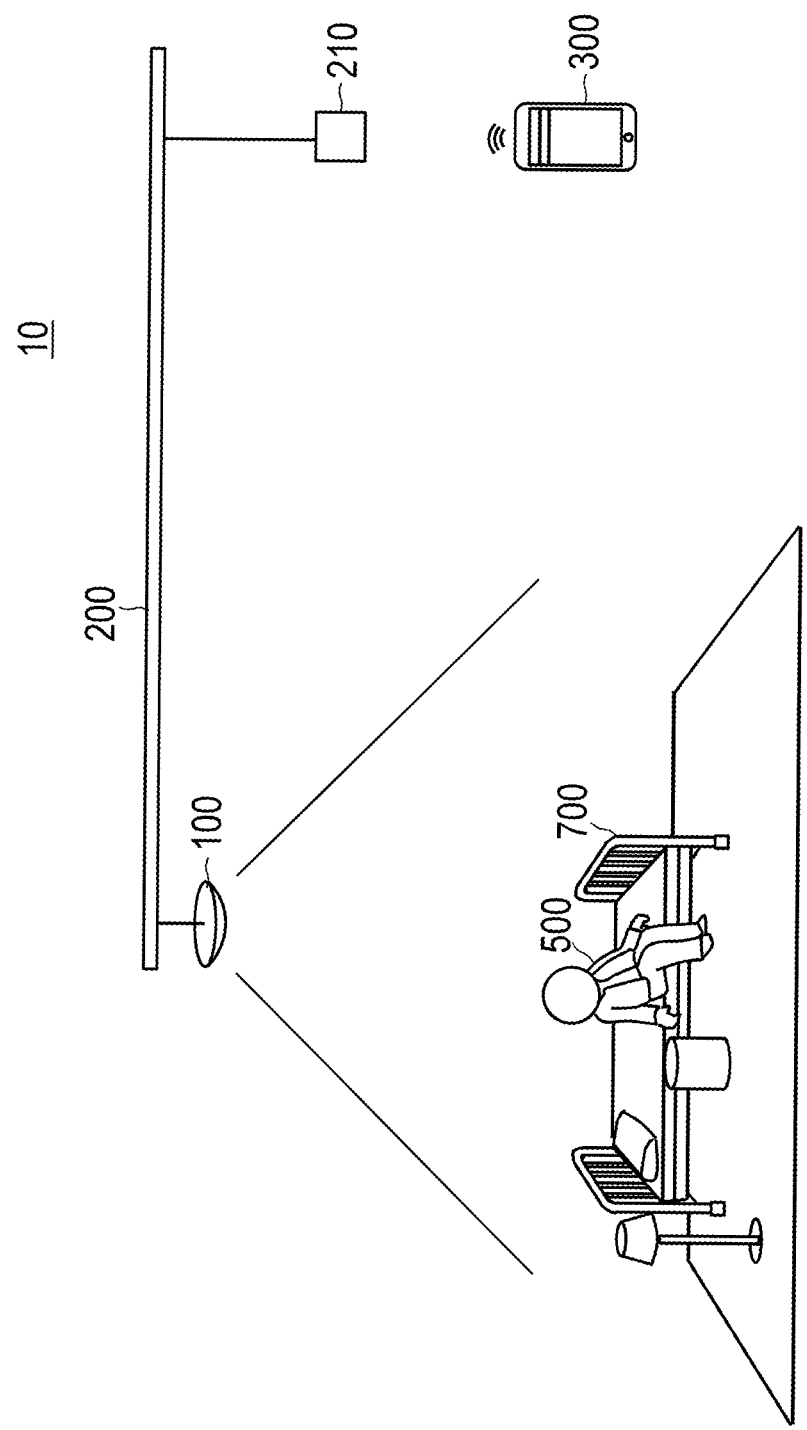
FIG. 1 is a diagram illustrating a schematic configuration of a posture estimation system according to one or more embodiments.

FIG. 1 is a diagram illustrating a schematic configuration of a posture estimation system 10.

The posture estimation system 10 includes a detector 100, a communication network 200, and a mobile terminal 300. The detector 100 is included in the posture estimation device and the behavior estimation device, and is connected to the mobile terminal 300 through the communication network 200 via an access point 210 in a mutually communicable manner. The detector 100 can be a single integrated device, or can be a plurality of devices to be arranged separately. Note that a server (not illustrated) that can mutually communicate with the detector 100 and the mobile terminal 300 through the communication network 200 may be provided, and the server may perform a part of the functions of the detector 100.

The detector 100 is disposed on the ceiling or the like of a room of a subject 500 (subject). The subject 500 is, for example, a person who needs care or nursing by a staff or the like. The detector 100 captures an image of a predetermined observation area to obtain an image (hereinafter also simply referred to as "captured image 505" (see FIG. 4 etc.)), and detects the subject 500 included in the captured image 505 as a person. The detector 100 detects an area in which an object is present in the captured image 505, and estimates a category of the object included in the detected area, thereby detecting the subject 500. The area in which the object is present is detected as a candidate rectangle including the object in the captured image 505. Among the detected candidate rectangles, a candidate rectangle in which the category of the object is estimated to be a person is detected as a human rectangle 510 (see FIG. 7), thereby detecting the subject 500. The detector 100 further detects (estimates) a head rectangle 520 (see FIG. 8) and joint points 530 (See FIG. 8) on the basis of the human rectangle 510. Although details will be described later, the detector 100 further calculates a feature amount of the subject 500 on the basis of the human rectangle 510, the head rectangle 520, and the joint points 530. The human rectangle 510, the head rectangle 520, and the joint points 530 that indicate features of the subject 500 and serve as a basis for calculating the feature amount will also be referred to as "detected information" hereinafter. The detector 100 switches, on the basis of a geometric relationship between the detector 100 (more specifically, the camera) and the subject 500, a model parameter for estimating a posture of the subject 500 from time-series feature amounts by machine learning, and estimates the posture of the subject 500 using the model parameter after the switching. Then, the detector 100 estimates behavior of the subject 500 on the basis of the estimated posture. Hereinafter, as an example, descriptions will be given on the assumption that the detector 100 estimates the posture of the subject 500 by machine learning using the hidden Markov model. The geometric relationship between the detector 100 and the subject 500 includes at least one of the position, orientation, and posture of the subject 500 with respect to the camera. Hereinafter, descriptions will be given on the assumption that the geometric relationship between the detector 100 and the subject 500 is the position of the subject 500 with respect to the camera, to simplify the descriptions.

The detector 100 can detect an event related to the subject 500 from the estimated posture and/or behavior. The event is a change in the state or situation related to the subject 500, which is, for example, an event to be reported (notified) to a staff member, such as getting up, getting out of bed, tumbling, falling, and abnormal micromotion. When the event is detected, the detector 100 transmits, to the mobile terminal 300, event notification for making notification on the content of the event.

The mobile terminal 300 is carried by the staff member or the like who performs care including caregiving and nursing for the subject 500. The mobile terminal 300 receives the event notification from the detector 100, and displays the content of the event notification, thereby notifying the staff member or the like of the occurrence of the event and the content thereof.

Figure 2:
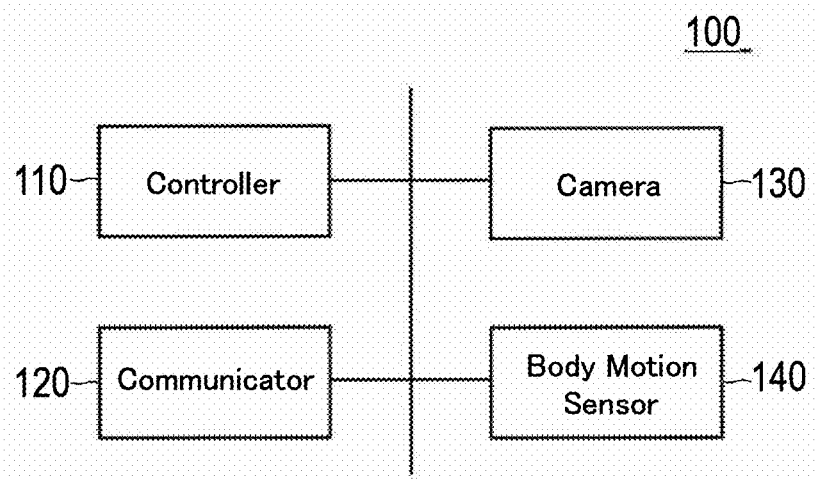
FIG. 2 is a block diagram illustrating a hardware configuration of a detector according to one or more embodiments.

FIG. 2 is a block diagram illustrating a hardware configuration of the detector 100. As illustrated in FIG. 2, the detector 100 includes a controller (processor) 110, a communicator 120, a camera 130, and a body motion sensor 140, which are mutually connected via a bus.

The controller 110 includes a CPU (Central Processing Unit) and a memory such as a RAM (Random Access Memory) and a ROM (Read Only Memory), and performs control of each unit of the detector 100 and arithmetic processing according to a program. Details of the function of the controller 110 will be described later.

The communicator 120 is interface circuitry (e.g., a LAN card, etc.) for communicating with the mobile terminal 300 or the like through the communication network 200.

The camera 130 is, for example, arranged on the ceiling of the room of the subject 500 or on the upper part of the wall, and captures the image of a range as wide as possible in the room of the subject 500 as a predetermined observation area, from a position where the subject 500 can be viewed from above, and outputs the captured image 505 (image data). The captured image 505 includes an image including the subject 500. The captured image 505 includes a still image and a moving image. The camera 130 can be a wide-angle camera. The wide-angle camera is a camera capable of taking the captured image 505 with a relatively wide angle of view, which is a camera in which the magnitude of distortion changes corresponding to the position in the captured image 505. The wide-range camera includes, for example, a fish-eye lens camera. The camera 130 may be a camera for wide-area shooting with an angle of view set to be wider by adjusting the installation height of the camera or the like so that a relatively wide range is set as an imaging range. The camera for wide-area shooting is a camera that takes the captured image 505 in which a ratio between the size of the object in the captured image 505 and the actual size of the object changes corresponding to the distance from the camera to the object in the photographing direction. A general camera in which the magnitude of the distortion is not changed corresponding to the position in the captured image 505 can be used as the camera for wide-area shooting. Although the camera 130 is a near-infrared camera, a visible light camera may be used instead of this, or those cameras may be used in combination.

Figure 3:
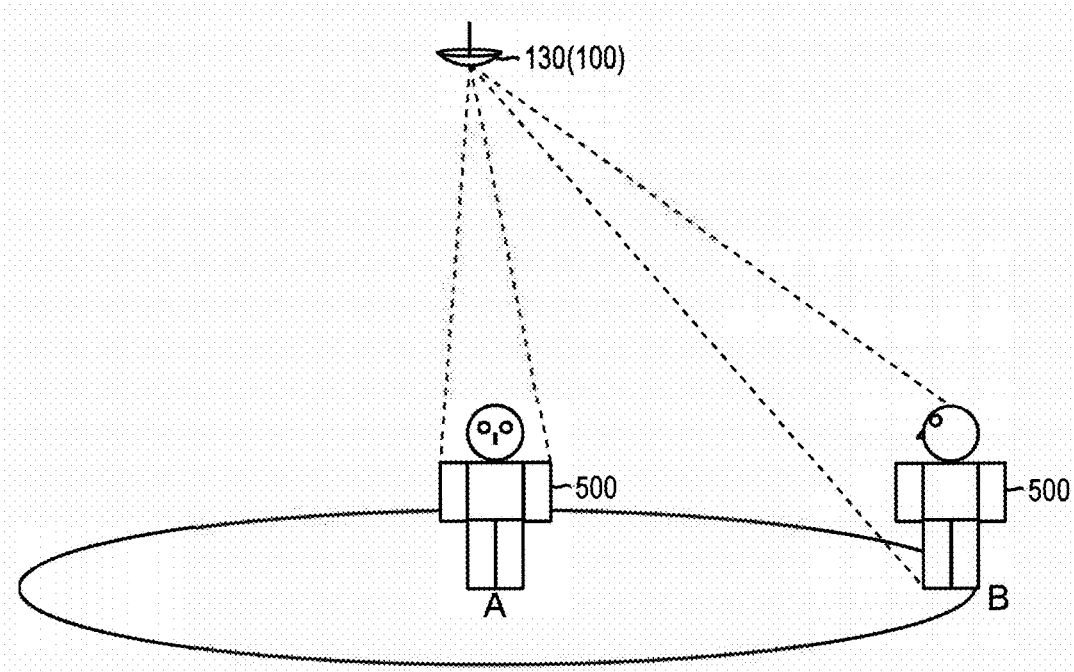
FIG. 3 is an explanatory diagram illustrating a positional relationship between a camera and a subject according to one or more embodiments.
Figure 4:
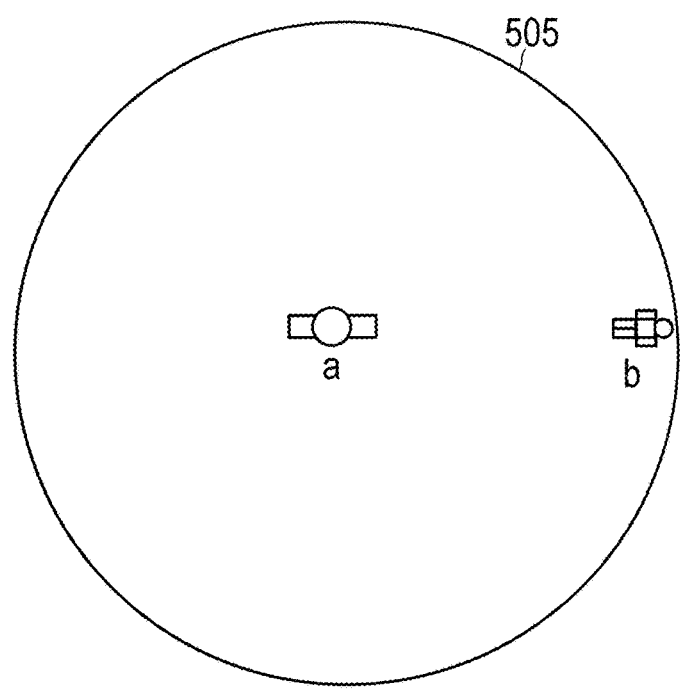
FIG. 4 is an explanatory diagram illustrating a captured image according to one or more embodiments.
Figure 5:
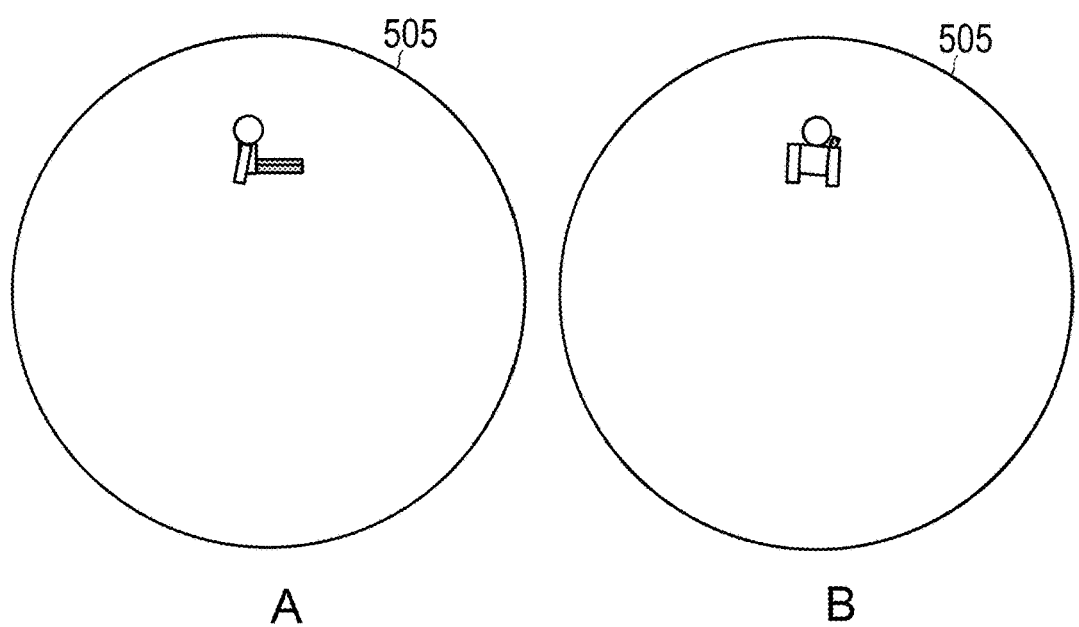
FIG. 5 is an explanatory diagram for illustrating how appearance of the subject changes depending on orientation and a posture of the subject with respect to the camera according to one or more embodiments.

FIG. 3 is an explanatory diagram illustrating a positional relationship between the camera 130 and the subject 500. FIG. 4 is an explanatory diagram illustrating the captured image 505. FIG. 5 is an explanatory diagram for illustrating how appearance of the subject 500 changes depending on orientation and a posture of the subject 500 with respect to the camera. In FIGS. 4 and 5, the captured image 505 taken by the wide-angle camera is illustrated. In the following descriptions, as an example, descriptions will be given on the assumption that the captured image 505 is an image captured by the wide-angle camera.

In FIG. 3, the subject 500 at a position A directly below the camera 130 is imaged at a position of the captured image 505 in FIG. 4. Since the subject 500 at the position A is close to the camera 130 in the captured image 505, the head and shoulders appear relatively large, and the arms and legs are hidden by the shoulders. Although the subject 500 at a position B appear to be small as it is far from the camera 130, the whole body appears. In the example A in FIG. 5, the orientation of the subject 500 with respect to the camera 130 is lateral, whereby the legs of the subject 500 in the floor sitting posture appear without being hidden by the upper body. On the other hand, in the example B in FIG. 5, the orientation of the subject 500 with respect to the camera 130 is backward-facing, whereby the legs of the subject 500 in the floor sitting posture are hidden by the upper body and the most part does not appear. In this manner, appearance (visible appearance) of the subject 500 in the captured image 505 changes depending on the position, orientation, and posture of the subject 500 with respect to the camera 130.

Figure 6:
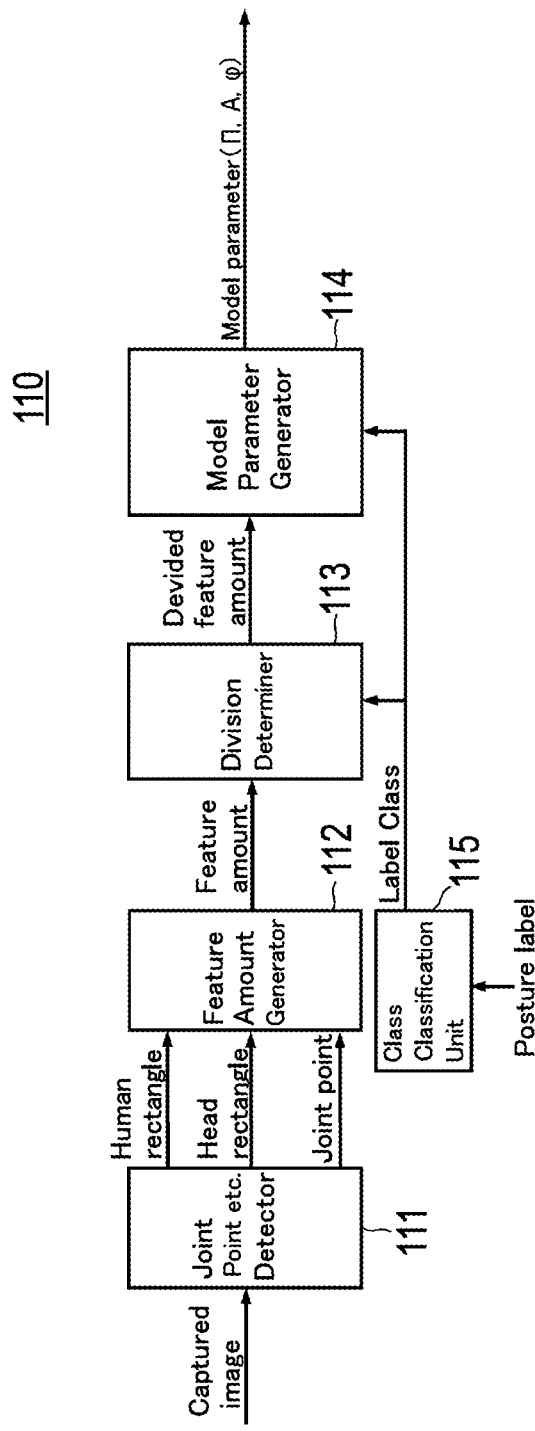
FIG. 6 is a functional block diagram illustrating functions of a controller during learning for posture estimation by using machine learning according to one or more embodiments.

FIG. 6 is a functional block diagram illustrating functions of the controller 110 during learning for posture estimation by using machine learning.

As illustrated in FIG. 6, at the time of learning, the controller 110 functions as a joint point etc. detector 111, a feature amount generator 112, a division determiner 113, a model parameter generator 114, and a class classification unit 115.

The joint point etc. detector 111 detects, from the captured image 505, the area in which the object is present in the captured image 505 as a candidate rectangle, and calculates a reliability score for each category included in the detected candidate rectangle. The joint point etc. detector 111 detects a candidate area having the highest reliability score of a human category as the human rectangle 510.

The joint point etc. detector 111 detects, as the head rectangle 520, an area including the head of the subject 500 from the human rectangle 510.

The joint point etc. detector 111 detects the joint points 530 of the subject 500 from the human rectangle 510.

The joint point etc. detector 111 can detect the human rectangle from the captured image 505 using a neural network (hereinafter referred to as "NN") reflected a dictionary (model parameter) for detecting the human rectangle 510 from the captured image 505. The joint point etc. detector 111 can detect the head rectangle 520 from the human rectangle 510 using an NN reflected a dictionary for detecting the head rectangle 520 from the human rectangle 510. The joint point etc. detector 111 can detect the joint points 530 of the subject 500 using an NN reflected a dictionary for detecting the joint points 530 of the subject 500 from the human rectangle 510.

The joint point etc. detector 111 can output the human rectangle 510 as a combination of the captured image 505 and coordinates of two facing vertices of the human rectangle 510. The joint point etc. detector 111 can output the head rectangle 520 as a combination of the captured image 505 and coordinates of two facing vertices of the head rectangle 520. The joint point etc. detector 111 can output the joint points 530 as respective coordinates in the captured image 505. The human rectangle 510, the head rectangle 520, and the joint points 530 are associated with each other for each frame of the captured image 505.

The joint point 530 detected at the time of learning is associated with a posture label by being given the posture label by a user. The posture label is a correct answer of the posture corresponding to the joint points 530. The posture label is a label indicating, for example, any one of the postures of a "standing posture", "sitting posture", and "lying posture".

The class classification unit 115 classifies posture labels associated with the human rectangle 510 into, for example, three label classes. The label classes are numerical values of 1 to 3, which correspond to the "standing posture", "sitting posture", and "lying posture" of the posture labels, respectively.

The joint points 530 detected at the time of learning are used as teaching data for learning together with the label classes corresponding to the posture labels assigned to the respective joint points 530.

Figure 7:
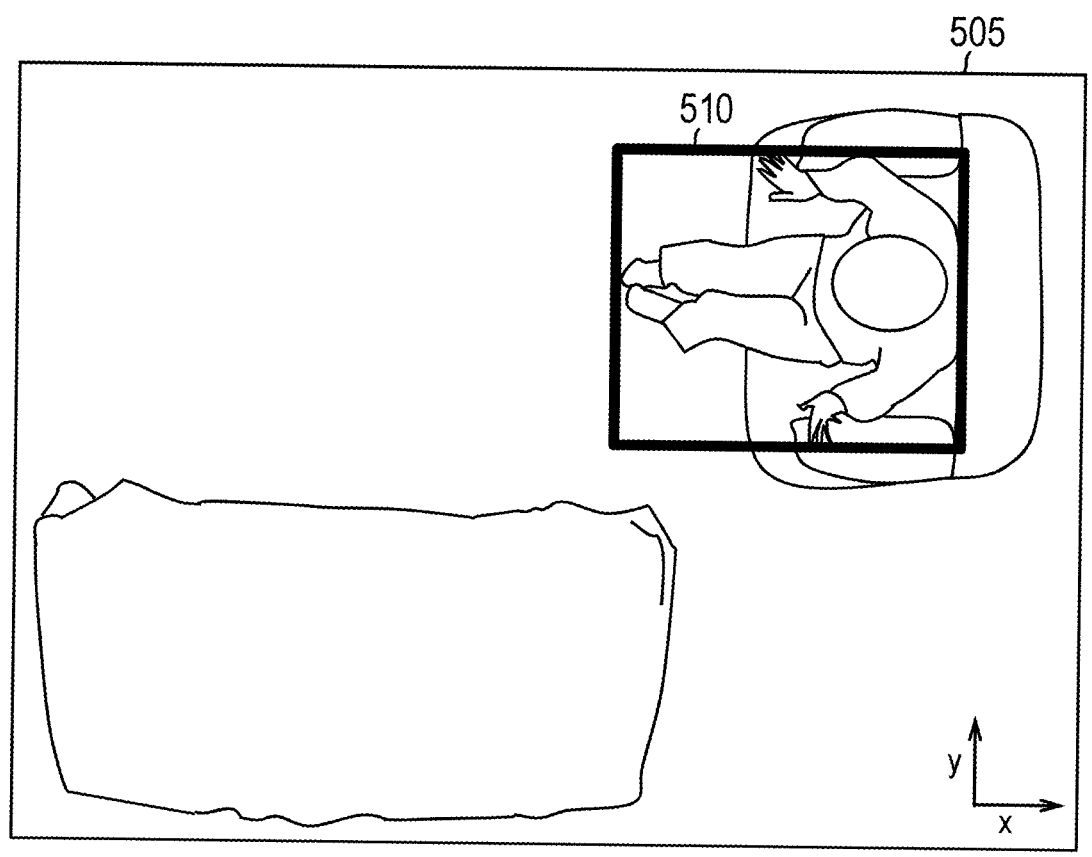
FIG. 7 is a schematic diagram illustrating a human rectangle according to one or more embodiments.

FIG. 7 is a schematic diagram illustrating the human rectangle 510.

In FIG. 7, the human rectangle 510 including the subject 500 in the sitting posture on a chair, which is detected from the captured image 505, is illustrated as an area within a thick-line rectangular frame.

Figure 8:
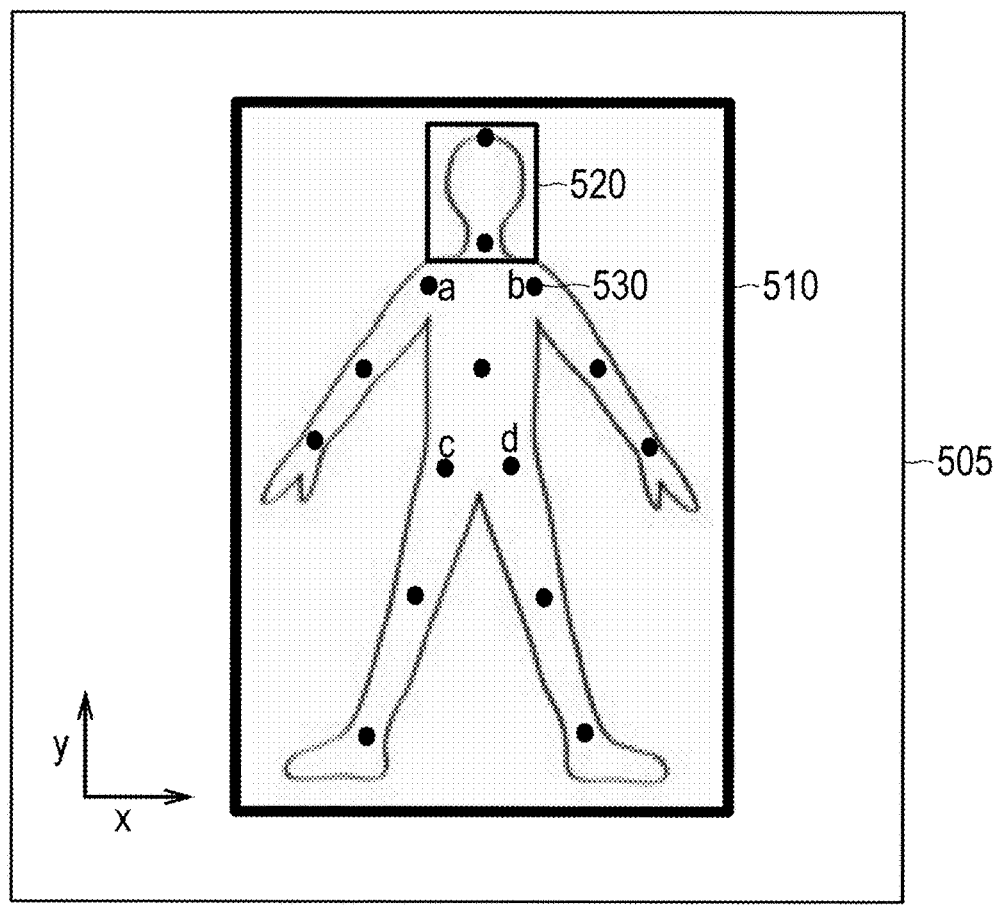
FIG. 8 is a schematic diagram illustrating a human rectangle, a head rectangle, and joint points according to one or more embodiments.

FIG. 8 is a schematic diagram illustrating the human rectangle 510, the head rectangle 520, and the joint points 530.

In FIG. 8, the human rectangle 510 including the subject 500 in the standing posture is illustrated as an area within a thick-line rectangular frame, and the head rectangle 520 is illustrated as an area within a thin-line rectangular frame. The joint points 530 are illustrated as black dots. Among the joint points 530, "a" indicates the right shoulder, "b" indicates the left shoulder, "c" indicates the right waist, and "d" indicates the left waist of the joint points 530, respectively.

The feature amount generator 112 calculates the feature amount of the subject 500 on the basis of at least one of the human rectangle 510, the head rectangle 520, and the joint points 530. The feature amount includes, for example, a center-of-gravity distance between the upper body and the lower body and the like.

Returning to FIG. 6, descriptions continue.

The division determiner 113 calculates the distance between the position of the human rectangle 510 in the captured image 505 (e.g., coordinates of the center of the human rectangle 510) and the center of the captured image 505 as a distance between the camera 130 and the subject 500 (hereinafter also referred to as a "distance to the subject 500"). Furthermore, the division determiner 113 calculates an index corresponding to the geometric relationship between the detector 100 (more specifically, camera 130) and the subject 500, thereby dividing (classifying) the feature amount for each index. The indices are, for example, a "short distance", an "intermediate distance", and a "far distance", more specifically the indices can be numerical values (e.g., 1 to 3) corresponding to those distances, specifically. That is, the division determiner 113 calculates the index to divide (classify) the feature amount into any one of the distance categories of the "short distance", "intermediate distance", and "far distance" (hereinafter also simply referred to as "distance category") for each index. Accordingly, the label class associated with the divided feature amount is also divided together with the feature amount.

In a case where the geometric relationship between the detector 100 and the subject 500 is the orientation of the subject 500 with respect to the camera 130, the division determiner 113 determines, for example, whether the subject 500 is "backward-facing" or "frontward-facing" with respect to the camera 130 as the index corresponding to the geometric relationship between the detector 100 and the subject 500. Specifically, the index can be a numerical value (e.g., 1 or 2) corresponding to whether it is backward-facing or frontward-facing with respect to the camera 130. Whether the subject 500 is "backward-facing" or "frontward-facing" with respect to the camera 130 can be estimated from a relative positional relationship between, among the joint points 530, the shoulder joint points (a and b (see FIG. 8)) and the waist joint points (c and d (see FIG. 8)). Note that, in a case where orientation of the subject 500 other than the "backward-facing" and "frontward-facing" (e.g., oblique orientation with respect to the camera 130) is used as an index, the index can be calculated further in consideration with the angle of the line segment connecting the shoulder joint points (a and b). The division determiner 113 divides (classifies) the feature amount into either the "backward-facing" or "frontward-facing" orientation category for each index by calculating the index. Accordingly, the label class associated with the divided feature amount is also divided together with the feature amount.

In a case where the geometric relationship between the detector 100 and the subject 500 is the posture of the subject 500, the division determiner 113 determines, for example, whether the posture of the subject 500 is the "standing posture", "sitting posture", or "lying posture" as an index corresponding to the geometric relationship between the detector 100 and the subject 500. Specifically, the indices can be numerical values (e.g., 1 to 3) corresponding to the respective postures of "standing posture", "sitting posture", and "lying posture". The index can be calculated (estimated) by a publicly known technique using an NN for estimating a posture from the human rectangle 510. The division determiner 113 divides (classifies) the feature amount into any of the posture categories of "standing posture", "sitting posture", and "lying posture" for each index by calculating the index. Accordingly, the label class associated with the divided feature amount is also divided together with the feature amount.

Figure 9:
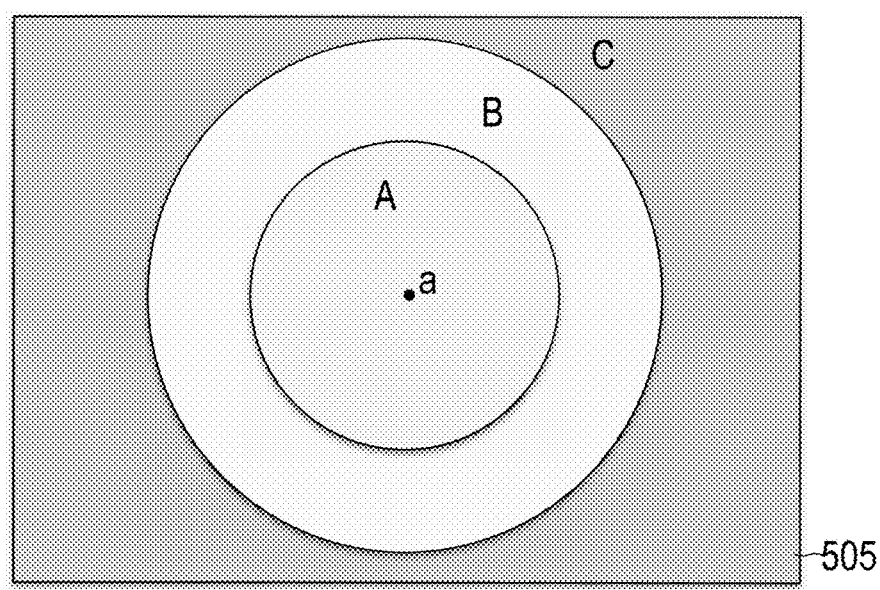
FIG. 9 is an explanatory diagram for illustrating distance categories according to one or more embodiments.

FIG. 9 is an explanatory diagram for illustrating the distance categories.

The center "a" of the captured image 505 corresponds to a position directly below the camera 130. In the example of FIG. 9, the distance category of the short distance including the center "a" of the captured image 505 corresponds to the area denoted by A. In addition, the distance category of the intermediate distance corresponds to the area denoted by B, and the distance category of the far distance corresponds to the area denoted by C.

The model parameter generator 114 performs learning for each distance category using the divided feature amount and the label class associated with the feature amount as teaching data. The model parameter generator 114 outputs model parameters π, A, and φ for each distance category generated by the learning.

Figure 10A:
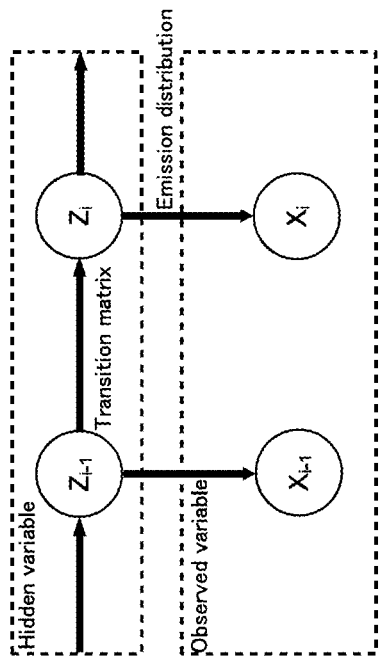
FIG. 10A is a schematic diagram of a general hidden Markov model according to one or more embodiments.
Figure 10B:
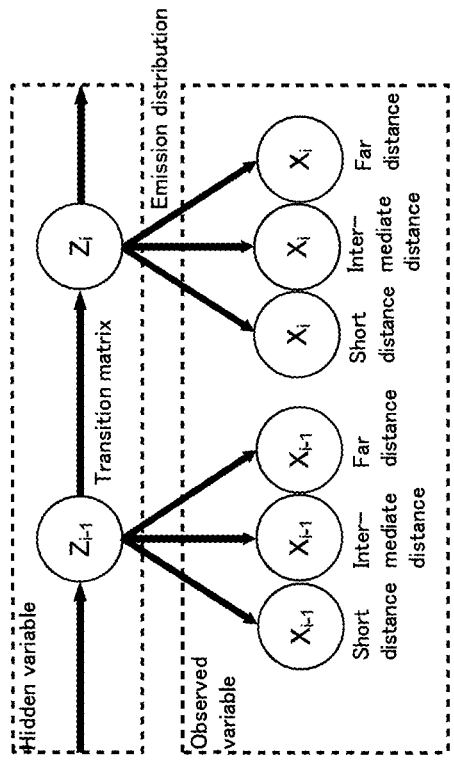
FIG. 10B is an explanatory diagram for illustrating leaning for each distance category using a hidden Markov model according to one or more embodiments.

FIG. 10A, 10B are explanatory diagrams for illustrating the leaning for each distance category using a hidden Markov model.

FIG. 10A is a schematic diagram of a general hidden Markov model.

The hidden Markov model is a model that estimates a series of hidden variables (latent variables) $z_i$ on the basis of an observed variable $x_i$. The feature amount corresponds to the observed variable $x_i$, and the label class corresponds to the hidden variable $z_i$. The letter "i" is a frame number of the captured image captured in a time series, and the frame is indicated to be an earlier frame as the number is smaller.

The joint probability distribution p (X, Z) of the observed variable x and the hidden variable z based on the hidden Markov model is given by the following formula.

$$p(X, Z) = \left\{ p(z_i) \prod_{i=2}^{N} p(z_i | z_{i-1}) \right\} \left\{ \prod_{i=1}^{N} p(x_i | z_i) \right\} \quad \text{[Formula 1]}$$

In the above formula, $p(z_1)$ indicates a probability in the initial state. "$p(z_i|z_{i-1})$" indicates a transition probability to the hidden variable $z_i$ of the frame (i) when the hidden variable $z_{i-1}$ of the frame (i−1) is set to be a condition in a time series. "$p(z_i|z_i)$" indicates an emission probability to the observed variable $x_i$ when the hidden variable $z_i$ is set to be a condition.

The above formula can be expressed as the following formula.

$$p(X, Z | \pi, A, \varphi) = \left\{ \pi_{z_i} \prod_{i=2}^{N} A_{z_{i-1}, z_i} \right\} \left\{ \prod_{i=1}^{N} p(x_i | \varphi_i) \right\} \quad \text{[Formula 2]}$$

In the above formula, πZ1(π) indicates a model parameter describing the initial state. "A" is a model parameter describing a transition probability of the hidden variable. "φ" is a model parameter describing an emission probability (output probability) (hereinafter referred to as "output probability parameter").

In the learning using the hidden Markov model, known values of the observed variable xi and the hidden variable zi are learned as teaching data, thereby estimating (generating) the model parameters π, A, and φ. Specifically, the model parameters π, A, and φ that maximizes the probability in which a combination of known values of the observed variable xi and the hidden variable zi, which is educator data, is generated in the joint probability distribution of the observed variable xi and the hidden variable zi expressed by the above formula are estimated (maximum likelihood estimation method).

In the estimation using the general hidden Markov model illustrated in FIG. 10A, the hidden variable zi is estimated from the observed variable xi using the model parameters π, A, and φ generated by the learning.

FIG. 10B is a schematic diagram of the hidden Markov model according to one or more embodiments.

As illustrated in FIG. 10B, in one or more embodiments, output probability parameters φA, φB, and φC are generated for each distance category by learning carried out for each distance category. φA is an output probability parameter generated by learning using teaching data of the distance category of "short distance". φB is an output probability parameter generated by learning using teaching data of the distance category of "intermediate distance". φC is an output probability parameter generated by learning using teaching data of the distance category of "far distance". In each learning, the divided feature amount obtained by being divided for each distance category and the label class associated with the feature amount are used as the teaching data.

In the estimation according to one or more embodiments, the label class that is the hidden variable zi is estimated for each distance category from the feature amount that is the observed variable xi using the learned model parameters π, A, and φ (with regard to φ, any one of φA, φB, and φC depending on the distance category) learned for each distance category.

The reason why the label class is estimated from the feature amount using the output probability parameters φA, φB, and φC different for each distance category is as follows. Since the appearance of the subject 500 in the captured image 505 changes (see FIGS. 4 and 5) depending on the position of the subject 500 with respect to the camera 130 (i.e., distance to the subject 500), the feature amount changes relatively largely depending on the distance to the subject 500. For that reason, if the same output probability parameter φ is used regardless of the distance to the subject 500, the posture estimation accuracy may decrease. Note that, since the model parameters 7E and A do not depend on the appearance (visible appearance) of the subject 500 in the captured image 505, it is not necessary to use different model parameters 7E and A for each distance category.

Figure 11:
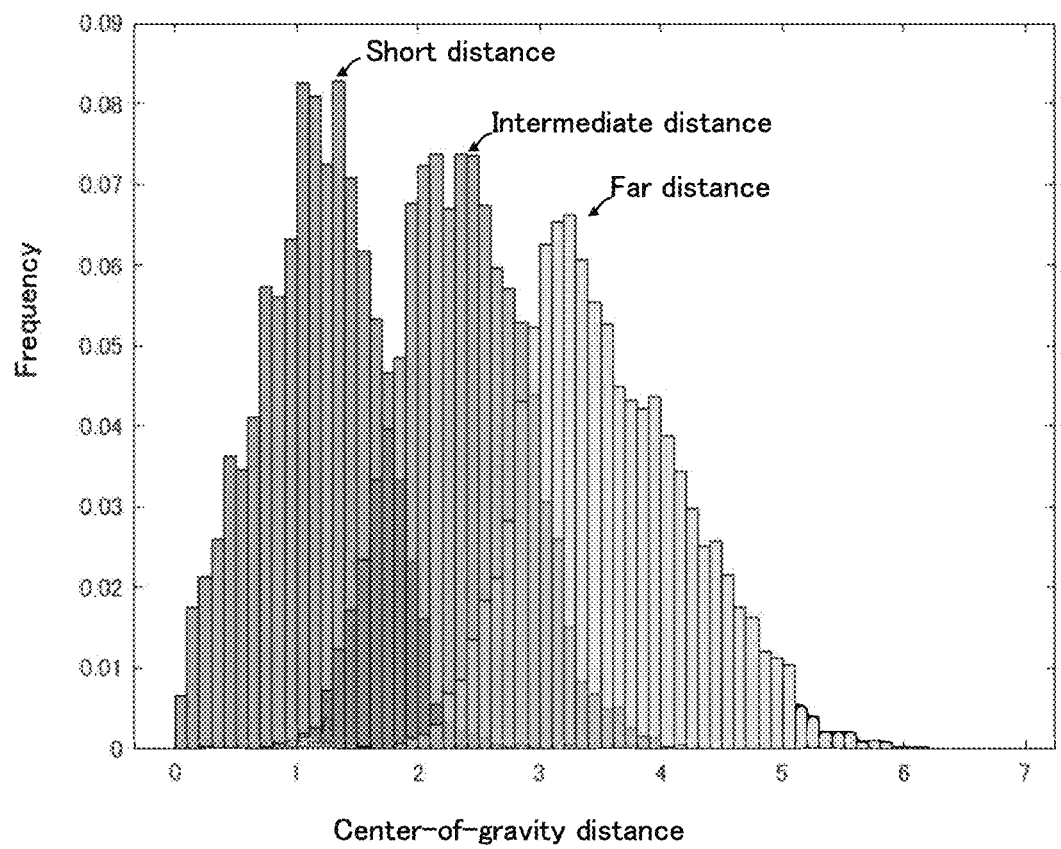
FIG. 11 is a graph illustrating distribution of a center-of-gravity distance between the upper body and the lower body, which is a feature amount, with respect to a distance to the subject according to one or more embodiments.

FIG. 11 is a graph illustrating distribution of the center-of-gravity distance between the upper body and the lower body, which is a feature amount, with respect to the distance to the subject 500. Distribution illustrated in relatively dark gray indicates the distribution of the distance category of the short distance, distribution illustrated in relatively light gray indicates the distribution of the far distance, and distribution illustrated in intermediate dark gray indicates the distribution of the intermediate distance.

In the example of FIG. 11, three peaks appear corresponding to the respective distance categories, and each of the distance categories has substantially normal distribution centered on the peak. The reason why the distribution is clearly distinguished for each distance category in this manner is that the distance categories are set appropriately.

The distance category can be determined by confirming the distribution of the actually divided data (e.g., teaching data) with reference to a theoretical value calculated from the optical projection relationship between the camera 130 and the subject 500. For example, the boundary between the intermediate distance and the far distance can be set the distance from the center of the captured image as a theoretical value in which the body axis length is reversed between the standing posture and the lying posture in the captured image.

Figure 12:
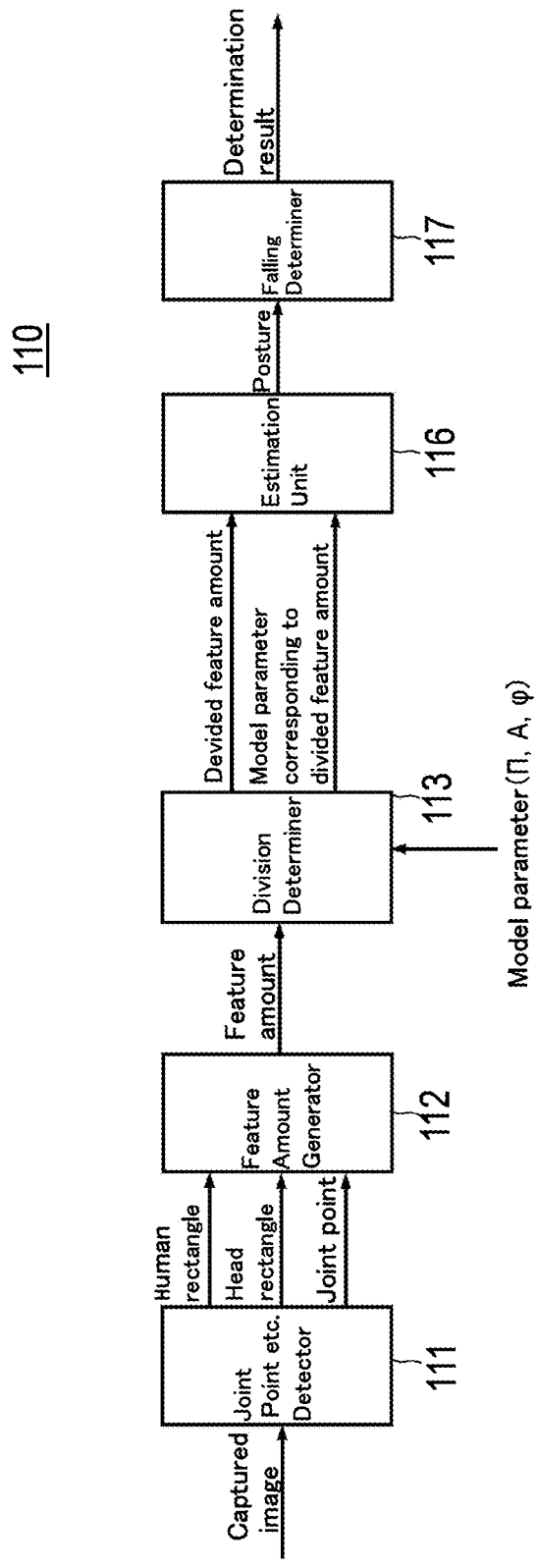
FIG. 12 is a functional block diagram illustrating functions of the controller at the time of posture estimation by using machine learning according to one or more embodiments.

FIG. 12 is a functional block diagram illustrating functions of the controller 110 at the time of posture estimation by using machine learning.

As illustrated in FIG. 12, at the time of estimation, the controller 110 functions as the joint point etc. detector 111, the feature amount generator 112, the division determiner 113, an inference unit 116, and falling determiner 117. The joint point etc. detector 111 is included in an acquisitor. The feature amount generator 112 is included in a feature amount calculator. The division determiner 113 is included in a switcher and an index calculator. The estimation unit 116 is included in a posture estimator. The falling determiner 117 is included in a behavior estimator.

The joint point etc. detector 111 and the feature amount generator 112 function at the time of estimation in a similar manner to the time of learning, and thus descriptions thereof will be omitted.

The division determiner 113 calculates the distance between the position of the human rectangle 510 in the captured image 505 (e.g., coordinates of the center of the human rectangle) and the center of the captured image 505 as a distance to the subject 500. Furthermore, the division determiner 113 calculates the index corresponding to the geometric relationship between the detector 100 and the subject 500, thereby dividing (classifying) the feature amount for each index. That is, the division determiner 113 calculates the index to divide (classify) the feature amount into any one of the distance categories of the "short distance", "intermediate distance", and "far distance" for each index. Accordingly, the label class associated with the divided feature amount is also divided together with the feature amount.

The division determiner 113 specifies, among the model parameters ((π, A, φA), (π, A, φB), and (π, A, φC)) for each distance category, a model parameter corresponding to the distance category of the divided feature amount.

The estimation unit 116 estimates, from the divided feature amount, a posture as one of the three classes of the "standing posture", "sitting posture", and "lying posture" (specifically, any one of the values of 1 to 3 corresponding to the three classes), for example, using the hidden Markov model to which the model parameter corresponding to the divided feature amount is applied and being specified by the division determiner 113.

The falling determiner 117 determines whether the subject 500 has fallen on the basis of the posture estimated by the estimation unit 116, and outputs a result of the determination. The falling determiner 117 determines that the subject 500 has fallen in a case where, for example, the standing posture and the lying posture are respectively estimated by the estimation unit 116 from the feature amounts generated from the frames that are consecutive in a time series. Alternatively, the falling determiner 117 may determine that the subject 500 has fallen down in a case where, for example, the sitting posture and the lying posture are respectively estimated by the estimation unit 116 from the feature amounts generated from the frames that are consecutive in a time series.

Note that the falling determiner 117 can also determine (estimate) behavior of the subject 500 other than falling. For example, it can determine (estimate) that the subject 500 is walking in a case where the standing posture is estimated by the estimation unit 116 from the respective feature amounts generated from the frames that are consecutive in a time series.

Figure 13:
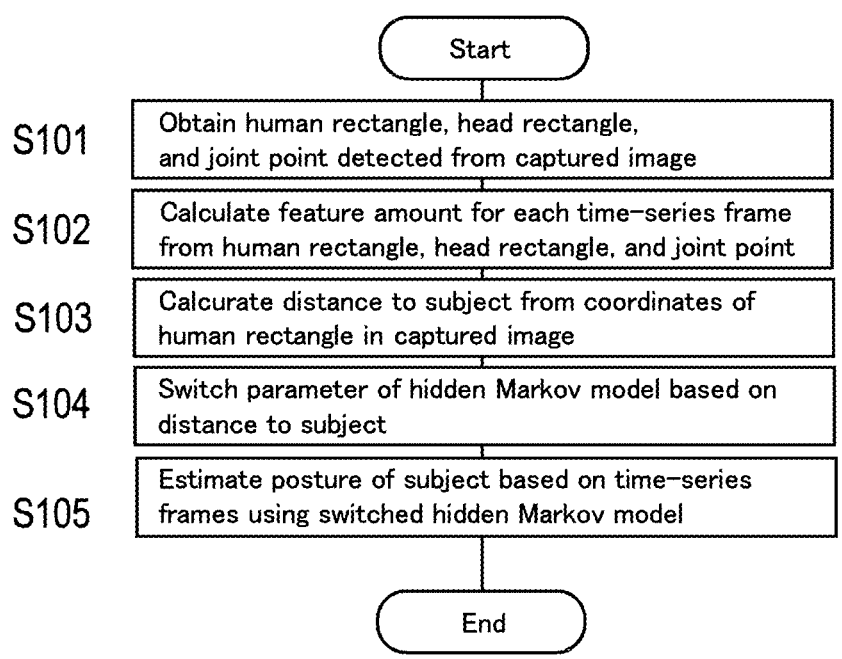
FIG. 13 is a flowchart illustrating operation of the detector according to one or more embodiments.

FIG. 13 is a flowchart illustrating operation of the detector 100. The flowchart is executed by the controller 110 in accordance with a program.

The controller 110 obtains the human rectangle 510, the head rectangle 520, and the joint points 530 detected from the captured image 505 (S101). The controller 110 estimates and obtains, from the captured image 505, the human rectangle 510, the head rectangle 520, and the joint points 530 by using machine learning using an NN.

The controller 110 calculates the feature amount for each time-series frame from at least one of the human rectangle 510, the head rectangle 520, and the joint points 530 (S102).

The controller 110 calculates the distance to the subject 500 from the coordinates of the human rectangle 510 in the captured image 505 (S103).

The controller 110 switches the model parameter of the hidden Markov model for estimating the posture to any of ($\pi$, A, $\varphi$A), ($\pi$, A, $\varphi$B), and ($\pi$, A, $\varphi$C) on the basis of the distance to the subject 500 (S104).

The controller 110 estimates, using the switched hidden Markov model, the posture of the subject 500 on the basis of time-series frames (S105).

One or more embodiments of the present invention exert the following effects.

A feature amount of the subject is calculated from predetermined detected information indicating the feature of the subject detected from a captured image captured by the imager from the position where the subject is viewed from above. Then, the model parameter for estimating, by machine learning, the posture of the subject from time-series feature amounts is switched on the basis of the geometric relationship between the imager and the subject. Accordingly, it becomes possible to improve detection accuracy of the posture or the like of the subject based on the captured image captured from the position where the subject is viewed from above.

Furthermore, estimating the posture of the subject using the hidden Markov model and the model parameter for calculating an output probability, of the hidden Markov model is switched on the basis of the geometric relationship between the imager and the subject. Accordingly, it becomes possible to improve detection accuracy of the posture or the like of the subject more easily and appropriately. In addition, even in a case where the subject moves from far to directly below the imager, it is possible to estimate the posture and behavior of the subject highly accurately in consideration of time series.

Furthermore, the geometric relationship is set to at least one of the position, orientation, and posture of the subject with respect to the imager, the index calculator for calculating the index corresponding to the geometric relationship is further provided, and the model parameter for estimating the posture of the subject on the basis of the index calculated by the index calculator is switched. Accordingly, it becomes possible to further improve the detection accuracy of the posture or the like of the subject.

For example, the predetermined detected information is set to at least one of the human rectangle, the head rectangle, and the joint points detected from the captured image. Accordingly, it becomes possible to calculate the feature amount of the subject efficiently and appropriately.

The configurations of the posture estimation device, the behavior estimation device, and the like described above are main configurations in describing characteristics of one or more embodiments, which are not limited to the configurations described above and various modifications can be made within the scope of the appended claims. In addition, a configuration of a general posture estimation device or the like is not excluded.

Furthermore, in the flowchart described above, a part of the steps may be omitted, or other steps may be added. In addition, a part of each step may be performed simultaneously, or one step may be divided into a plurality of steps and executed.

Furthermore, although the description has been made on the assumption that a posture or the like of a person is estimated in one or more embodiments, a posture or the like of an animal may be estimated.

Furthermore, the part of estimating the hidden variable (class) from the observed variable (feature amount) at the time of estimating the posture or the like of the subject 500 using the hidden Markov model may be replaced with machine learning using a neural network and executed.

In one or more embodiments, behavior such as falling is determined by the detector on the basis of the estimated posture, and a result of the determination is output. However, the determination of the behavior and the output of the determination result may not be performed by the detector, and a server communicably connected to the detector may receive the posture estimation result from the detector, determine behavior such as falling on the basis of the posture estimation result, and output the determination result.

In addition, the means and the method for performing various kinds of processing in the posture estimation system according to one or more embodiments can be achieved by either dedicated hardware circuitry or a programmed computer. The program may be provided by, for example, a computer-readable recording medium such as a USB memory and a DVD (Digital Versatile Disc)-ROM, or may be provided online via a network such as the Internet. In that case, the program recorded in the computer-readable recording medium is normally transferred to a storage unit, such as a hard disk, and stored therein. Moreover, the program may be provided as single application software, or may be incorporated into the software of the device, such as the detector, as one function.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A posture estimation device comprising:
a processor that:
obtains detected information indicating a feature of a subject, wherein the feature is detected based on an image that is captured by an imager from a position where the subject is viewed from above;
calculates, based on the obtained detected information, a center-of-gravity distance between an upper body and a lower body of the subject;
updates, based on a geometric relationship between the imager and the subject, a model parameter for estimating a posture of the subject by machine learning using the calculated center-of-gravity distance in a time series, wherein the geometric relationship is at least one of a position, orientation, and a posture of the subject with respect to the imager;
estimates the posture of the subject using the updated model parameter, and
detects, from the estimated posture, a change in a state or situation of the subject.

2. The posture estimation device according to claim 1, wherein
the processor further:
estimates the posture of the subject using a hidden Markov model, and
updates the model parameter for calculating an output probability of the hidden Markov model based on the geometric relationship between the imager and the subject.

3. The posture estimation device according to claim 1, wherein
the processor further calculates an index corresponding to the geometric relationship between the imager and the subject, and
the processor further updates the model parameter for estimating the posture of the subject based on the calculated index.

4. The posture estimation device according to claim 1, wherein
the detected information includes a human rectangle, a head rectangle, and a joint point detected from the image.

5. A behavior estimation device comprising:
the posture estimation device according to claim 1, wherein
the processor estimates behavior of the subject based on the estimated posture and detects the change from the estimated behavior.

6. A non-transitory computer-readable storage medium storing a posture estimation program that causes a computer to:
obtain detected information indicating a feature of a subject, wherein the feature is detected based on an image that is captured by an imager from a position where the subject is viewed from above;
calculate, based on the obtained detected information, a center-of-gravity distance between an upper body and a lower body of the subject;
update, based on a geometric relationship between the imager and the subject, a model parameter for estimating a posture of the subject by machine learning using the calculated center-of-gravity distance in a time series, wherein the geometric relationship is at least one of a position, orientation, and a posture of the subject with respect to the imager;
estimate the posture of the subject using the updated model parameter, and
detect, from the estimated posture, a change in a state or situation of the subject.

7. The non-transitory recording medium according to claim 6, wherein
the program further causes the computer to:
estimate the posture of the subject using a hidden Markov model, and
update the model parameter for calculating an output probability of the hidden Markov model based on the geometric relationship between the imager and the subject.

8. The non-transitory recording medium according to claim 6, wherein
the program further causes the computer to:
calculate an index corresponding to the geometric relationship between the imager and the subject, and
update the model parameter for estimating the posture of the subject based on the calculated index.

9. The non-transitory recording medium according to claim 6, wherein
the detected information includes a human rectangle, a head rectangle, and a joint point detected from the image.

10. A posture estimation method that causes a computer to execute a posture estimation program, the method comprising:
obtaining detected information indicating a feature of a subject, wherein the feature is detected based on an image that is captured by an imager from a position where the subject is viewed from above;
calculating, based on the obtained detected information, a center-of-gravity distance between an upper body and a lower body of the subject;
updating, based on a geometric relationship between the imager and the subject, a model parameter for estimating a posture of the subject by machine learning using the calculated center-of-gravity distance in a time series, wherein the geometric relationship is at least one of a position, orientation, and a posture of the subject with respect to the imager;
estimating the posture of the subject using the updated model parameter, and
detecting, from the estimated posture, a change in a state or situation of the subject.

11. The posture estimation method according to claim 10, further comprising:
estimating the posture of the subject using a hidden Markov model, and
updating the model parameter for calculating an output probability of the hidden Markov model based on the geometric relationship between the imager and the subject.

12. The posture estimation method according to claim 10, wherein
the method further comprising:
calculating an index corresponding to the geometric relationship between the imager and the subject, and
updating the model parameter for estimating the posture of the subject based on the calculated index.

13. The posture estimation method according to claim 10, wherein the detected information includes a human rectangle, a head rectangle, and a joint point detected from the image.

14. The posture estimation device according to claim 1, wherein
the processor further:
transmits, to a mobile terminal, event notification upon detecting the change.

15. The posture estimation device according to claim 1, wherein
the processor further:
detects the change as an event that requires event notification to a user, wherein the event includes at least one of getting up, getting out of bed, tumbling, falling, and abnormal micromotion.

16. The non-transitory recording medium according to claim 6, wherein
the program further causes the computer to:
detect the change as an event that requires event notification to a user, wherein the event includes at least one of getting up, getting out of bed, tumbling, falling, and abnormal micromotion.

17. The posture estimation method according to claim 10, wherein
the detecting includes:
detecting the change as an event that requires event notification to a user, wherein the event includes at least one of getting up, getting out of bed, tumbling, falling, and abnormal micromotion.

* * * * *